United States Patent [19]

Urban et al.

[11] Patent Number: 5,437,645
[45] Date of Patent: Aug. 1, 1995

[54] SURGICAL INSTRUMENT POSITIONING DEVICE

[75] Inventors: Carl T. Urban, Norwalk; Marc J. Theroux, Bethel; Kourash Azarbarzin, Ridgefield; Maria E. Lopez-Isa, Shelton; Andrew J. McCarthy; Csaba L. Rethy, both of Fairfield, all of Conn.

[73] Assignee: United States Surgical Corporation, Norwalk, Conn.

[21] Appl. No.: 134,121

[22] Filed: Oct. 8, 1993

[51] Int. Cl.⁶ ...................... A61M 5/178; A61M 5/32
[52] U.S. Cl. ..................................... 604/165; 604/178
[58] Field of Search ................. 128/DIG. 6, DIG. 26, 128/657, 772; 604/95, 174, 178–180, 165, 159; 606/206; 248/74.2

[56] References Cited

U.S. PATENT DOCUMENTS

| | | | |
|---|---|---|---|
| 2,478,595 | 8/1949 | Richter | 606/206 |
| 3,726,522 | 4/1973 | Silberman . | |
| 4,287,891 | 9/1981 | Peters . | |
| 4,360,025 | 11/1982 | Edwards . | |
| 4,392,857 | 7/1983 | Beran . | |
| 4,498,903 | 2/1985 | Mathew . | |
| 4,516,968 | 5/1985 | Marshall et al. . | |
| 4,593,681 | 6/1986 | Soni . | |
| 4,601,710 | 7/1986 | Moll . | |
| 4,615,692 | 10/1986 | Giacalone et al. . | |
| 4,632,671 | 12/1986 | Dalton . | |
| 4,670,008 | 6/1987 | Von Albertini . | |
| 4,735,615 | 4/1988 | Uddo, Jr. et al. | 604/178 |
| 4,890,626 | 1/1990 | Wang . | |
| 4,932,943 | 6/1990 | Nowak | 604/178 |
| 4,946,443 | 8/1990 | Hauser et al. . | |
| 4,955,864 | 9/1990 | Hajduch . | |
| 4,973,312 | 11/1990 | Andrew . | |
| 4,973,313 | 11/1990 | Katsaros et al. . | |
| 4,985,033 | 1/1991 | Boebel et al. . | |
| 5,009,227 | 4/1991 | Nieuwstad . | |
| 5,009,643 | 4/1991 | Reich et al. . | |
| 5,026,352 | 6/1991 | Anderson | 604/178 |
| 5,064,414 | 11/1991 | Revane . | |
| 5,069,206 | 12/1991 | Crosbie . | |
| 5,073,169 | 12/1991 | Raiken . | |
| 5,098,392 | 3/1992 | Fleischhacker et al. . | |
| 5,125,911 | 6/1992 | Grabenkort et al. . | |
| 5,137,520 | 8/1992 | Maxson et al. . | |
| 5,141,496 | 8/1992 | Dalto et al. . | |
| 5,167,630 | 12/1992 | Paul . | |
| 5,171,245 | 12/1992 | Cezana . | |
| 5,176,662 | 1/1993 | Bartholomew et al. . | |
| 5,188,609 | 2/1993 | Bayless et al. | 604/174 |
| 5,195,981 | 3/1993 | Johnson . | |
| 5,207,651 | 5/1993 | Snyder . | |
| 5,211,633 | 5/1993 | Stouder, Jr. . | |
| 5,217,441 | 6/1993 | Shichman . | |
| 5,221,264 | 6/1993 | Wilk et al. . | |
| 5,263,939 | 11/1993 | Wortrich | 604/174 |
| 5,263,944 | 11/1993 | Vidal et al. . | |
| 5,267,970 | 12/1993 | Chin et al. | 604/174 |
| 5,312,351 | 5/1994 | Gerrone | 604/264 |
| 5,312,375 | 5/1994 | Gurmarnik | 604/264 |

FOREIGN PATENT DOCUMENTS

| | | |
|---|---|---|
| 0232600 | 8/1987 | European Pat. Off. . |
| 0396882 | 11/1990 | European Pat. Off. . |
| 0485280 | 5/1992 | European Pat. Off. . |
| 0521590 | 1/1993 | European Pat. Off. . |
| 0538060 | 4/1993 | European Pat. Off. . |

OTHER PUBLICATIONS

Endopath* Trocar Reducers and Endopath* Adjustable Stability Threads, by Ethicon Distributor Price List ©; Feb. 24, 1992.
Endopath* Surgical Trocar Universal Reducer, pamphlet by Ethicon Endo-Surgery, ©1992.

Primary Examiner—C. Fred Rosenbaum
Assistant Examiner—Frank Wilkens, III

[57] ABSTRACT

A device for positioning a surgical instrument having an elongated portion, the device comprising a housing having an opening therethrough to receive the elongated instrument portion and an actuation member mounted to said housing and movable between a first position and a second position. The actuation member overlaps a portion of said opening in said second position to prevent movement of the elongated portion of the instrument. The actuation member may be movable along a plane parallel, perpendicular or lateral to a longitudinal axis of the surgical instrument.

13 Claims, 14 Drawing Sheets

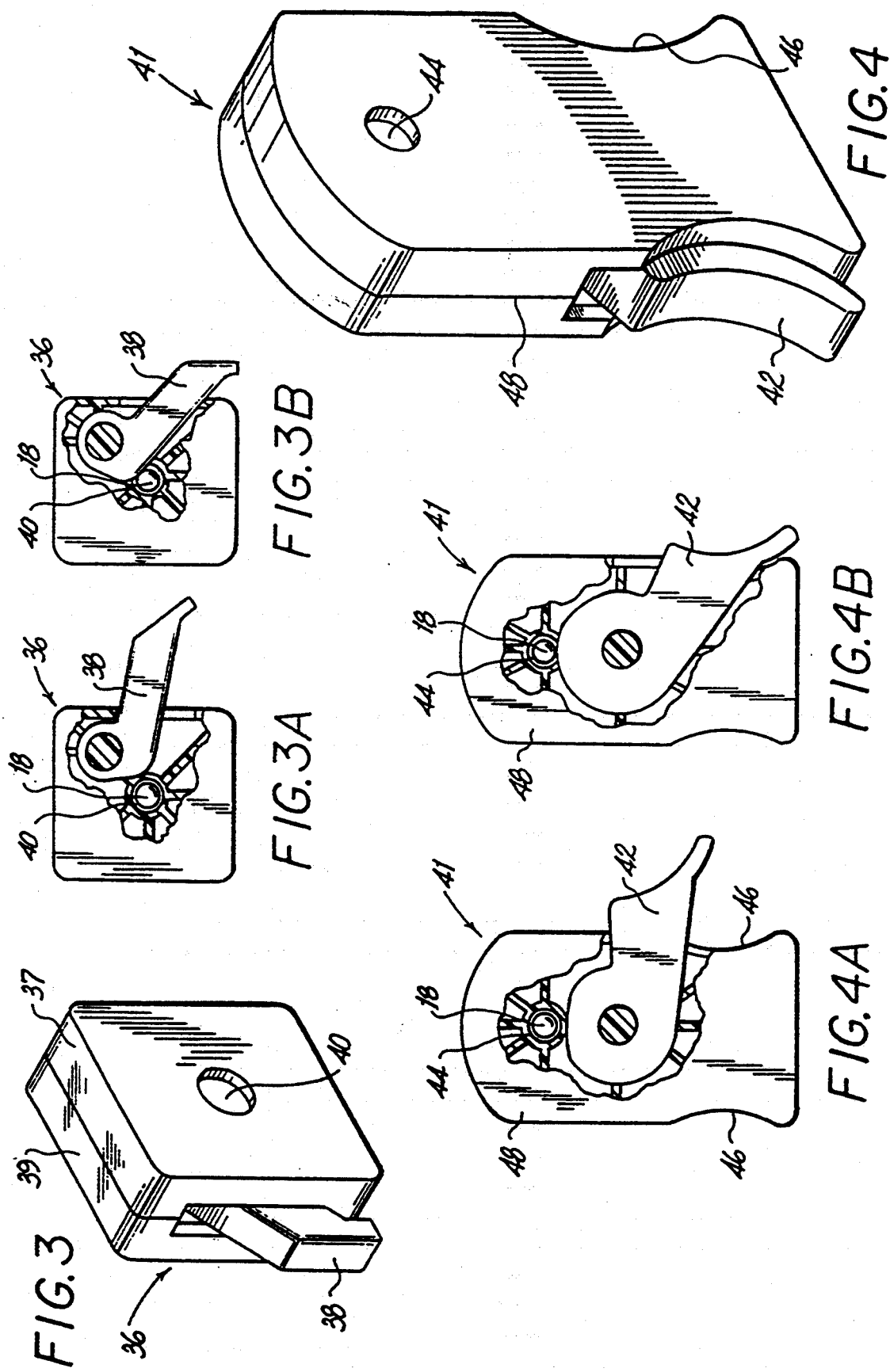

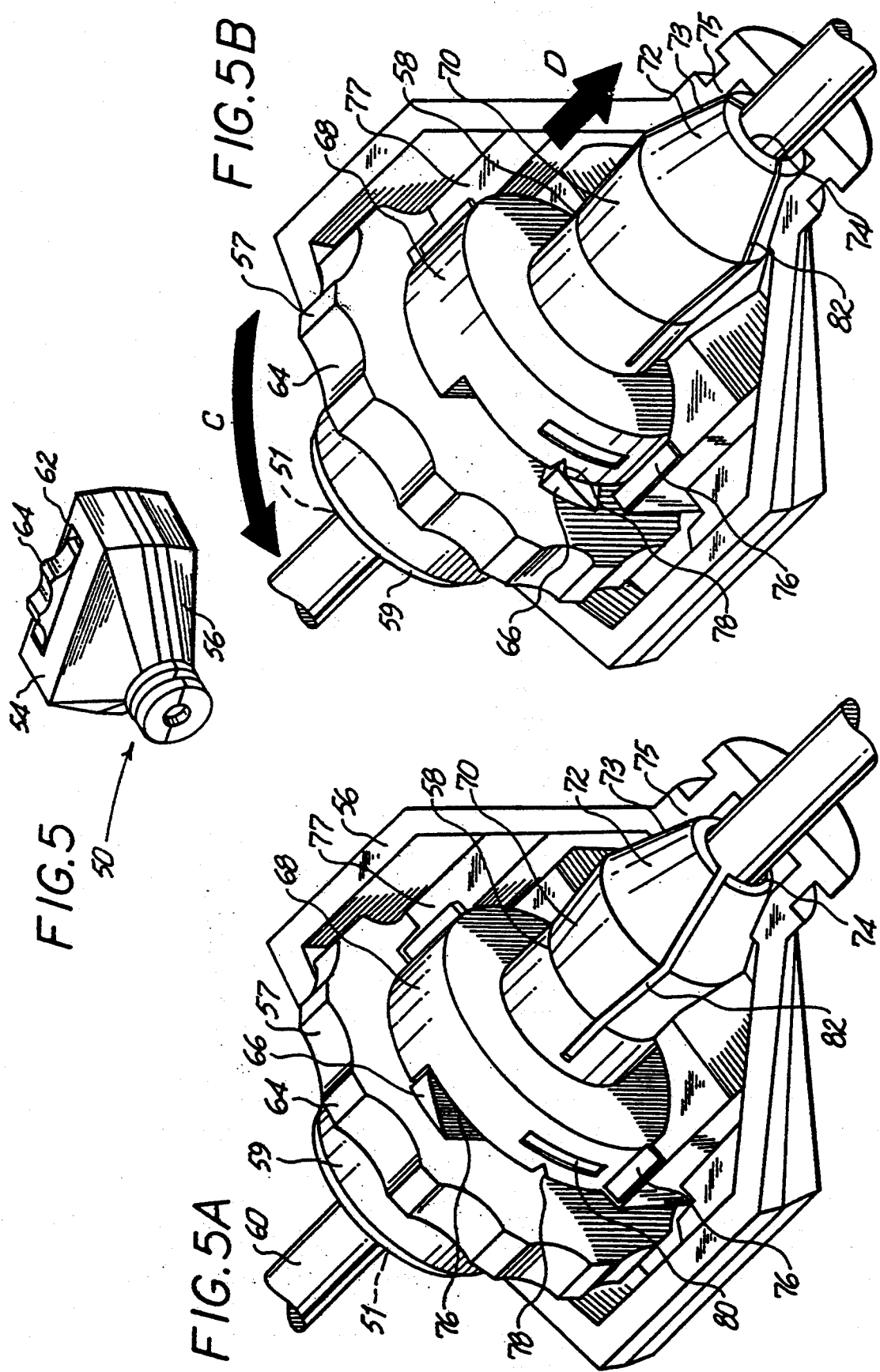

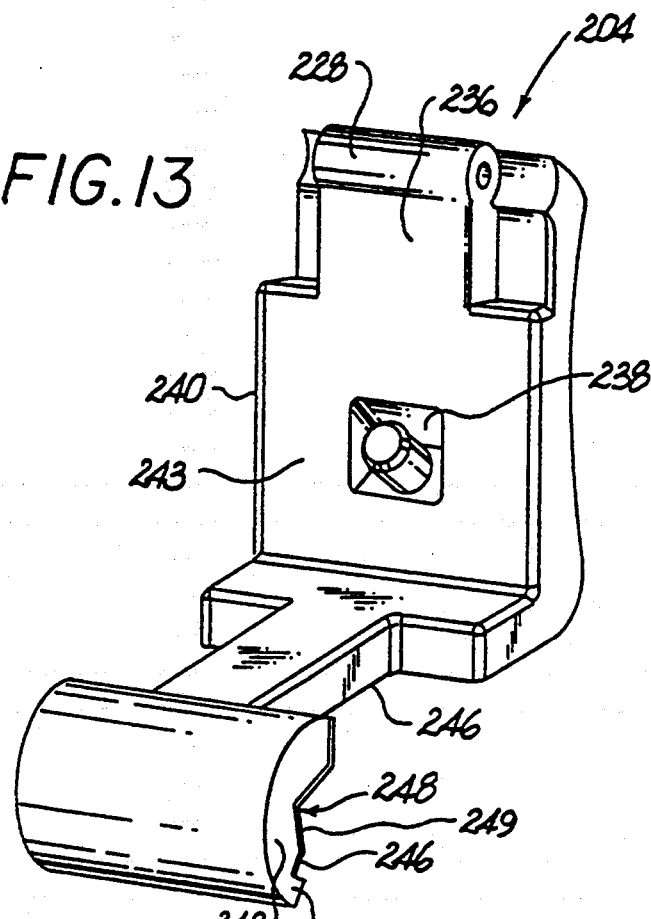
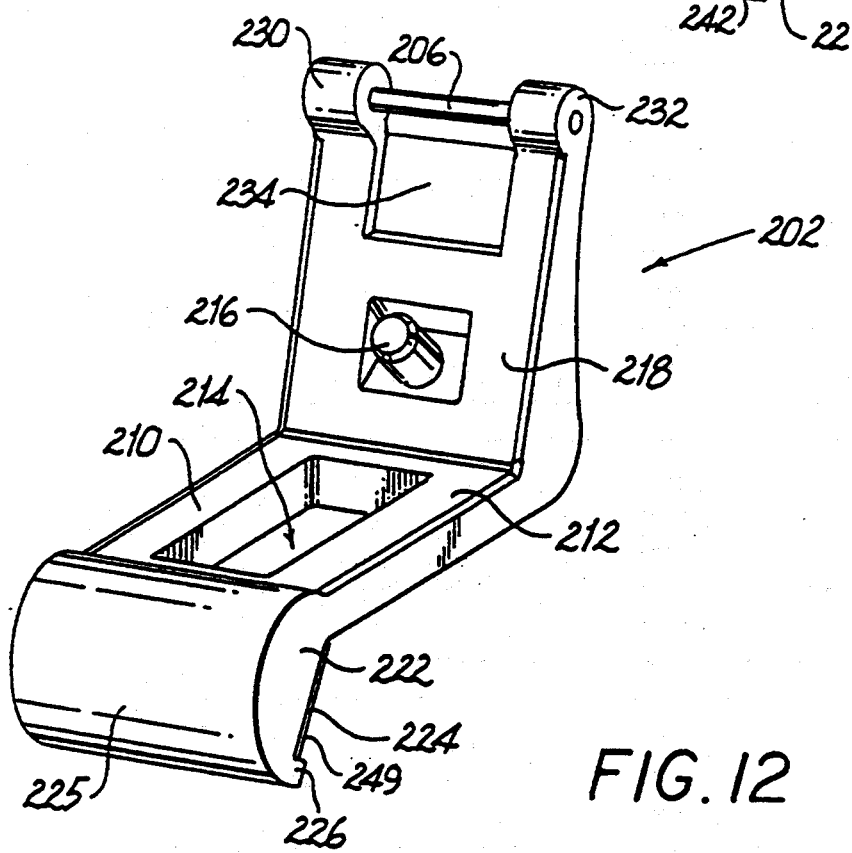

SURGICAL INSTRUMENT POSITIONING DEVICE

FIELD OF THE INVENTION

The invention relates to a device for positioning a surgical instrument, and more particularly to a device for locking the position of a surgical instrument during an endoscopic surgical procedure.

DESCRIPTION OF THE PRIOR ART

In endoscopic or laparoscopic procedures, surgery is performed through a small incision in the patient's body. The incision provides access for a trocar or cannula device which allows insertion of various surgical instruments including, for example, retractors, scissors, and clip appliers. In some surgical procedures, the surgical instrument is inserted directly through the small incision and into the body cavity. During endoscopic and other surgical procedures, it is often desired or necessary to lock the position of such a surgical instrument positioned in a body cavity. While several devices have been proposed for locking the position of a trocar or cannula device few instruments exist which are configured for locking the position of a surgical instrument inserted either through a trocar or cannula device, or directly through the incision itself.

One example of a device for locking the position or supporting a trocar is disclosed in U.S. Pat. No. 5,073,169 and includes a membrane having an aperture for receiving the trocar, an outer flange portion and a bellows-like portion positioned therebetween. The membrane of this device is adhered to the body and forms a substantially tight fit and seal with the trocar. A cannula skirt for immobilizing a cannula or sheath inserted into a body during a laparoscopic surgical procedure is disclosed in U.S. Pat. No. 5,137,520. In this device a torsional spring may be attached to the skirt around the skirt stem and adjusted to increase friction between the cannula and skirt to lock the cannula. Another device for positioning a trocar is disclosed in U.S. Pat. No. 5,217,441 and includes an inner housing which receives the trocar cannula and threadably engages an outer housing. Rotation of the inner housing causes gripping fingers positioned thereon to be cammed by a surface on the outer housing thereby locking the position of the trocar cannula.

Notwithstanding the foregoing disclosures, there presently exists a need for a surgical hand instrument locking device which provides convenient, reliable locking or positioning of such an instrument during an endoscopic surgical procedure. The present invention provides such a device for locking the position of a surgical instrument.

SUMMARY OF THE INVENTION

It is generally accepted that endoscopic procedures are more common than laparoscopic procedures. Accordingly, the subject invention shall be discussed in terms of endoscopic procedures and apparatus. However, use herein of terms such as "endoscopic", "endoscopically", and "endoscopic portion", among others, should not be construed to limit the present invention to an apparatus for use only in conjunction with an endoscopic tube. To the contrary, it is believed that the subject invention may find use in any procedure in which access is limited to a small incision, including but not limited to laparoscopic procedures.

In accordance with the present invention, a device for locking the position of a surgical instrument during a surgical procedure is provided. Each of these devices locks the position of the surgical instrument positioned therein by frictionally engaging the elongated portion of the surgical instrument.

In one embodiment, the device comprises a housing having an aperture extending therethrough, an actuation member mounted to the housing and a mounting assembly for mounting the device to a trocar. The housing aperture is configured and dimensioned to receive the elongated portion of a surgical instrument. The actuation member is movable between a first position in which the surgical instrument is unrestrained from longitudinal movement and a second locked position in which the actuation member selectively locks the surgical instrument by frictionally engaging a portion of the instrument.

The actuation member may be pivotable about an axis either parallel or perpendicular to the longitudinal axis of the surgical instrument. When pivoted, the actuation member engages the surgical instrument against an interior wall of the aperture thereby locking the position of the surgical instrument positioned therein. While the above device includes a mounting assembly for attachment to a trocar device, the features of the device could also be implemented directly into the trocar.

In another preferred embodiment, the actuation member is slidably mounted in the housing and includes a slot formed therein having at least two apertures, each with a different diameter. The first aperture slidably receives and permits longitudinal movement of the surgical instrument elongated portion and has a greater diameter than the second aperture which receives and locks the position of the surgical instrument by frictional engagement with the instrument elongated portion. The actuation member is movable within the housing between an unlocked position in which the first aperture of the actuation member is concentric with the housing aperture and a locked position in which the second aperture is concentric with the housing aperture. The position of the surgical instrument is locked by moving the actuation member from its unlocked position to its locked position such that second aperture frictionally engages the surgical instrument thereby locking its position. This embodiment could also be designed as an integral part of a trocar.

In yet a further embodiment, the device includes a pair of pivotally attached legs with a spring mounted to and extending between each of the legs. The legs are movable between an open position which allows placement of the device around the elongated portion of the surgical instrument and a locked position which locks the position of the surgical instrument relative to a trocar or other structure. The spring mounted within the legs biases the legs in their second position, but the legs are movable to the first position by overcoming the tension of the spring.

BRIEF DESCRIPTION OF THE DRAWINGS

The accompanying drawings, referred to herein and constituting a part hereof, illustrate preferred embodiments of the present invention, and together with the description, serve to explain the principles of the invention. The drawings may be briefly described as follows:

FIG. 3 is a perspective view of an alternative embodiment of a surgical instrument positioning device;

FIG. 3A is a partial cross-sectional view of a positioning device taken along line 3—3 of FIG. 3 shown in the unlocked position;

FIG. 3B is a partial cross-sectional view of the positioning device taken along line 3—3 FIG. 3 shown in the locked position;

FIG. 4 is a perspective view of another alternative embodiment of a surgical instrument positioning device;

FIG. 4A is a rear partial cross-sectional view of the surgical instrument positioning device taken along the line 4—4 of FIG. 4 shown in the unlocked position;

FIG. 4B is a rear partial cross-sectional view of the surgical instrument positioning device taken along the line 4—4 of FIG. 4 shown in the unlocked position;

FIG. 5 is a perspective view of yet another alternative embodiment of a surgical instrument positioning device;

FIG. 5A is a rear partial cross-sectional perspective view of a surgical instrument positioning device taken along the line 5—5 of FIG. 5 shown in the locked position;

FIG. 5B is a rear partial cross-sectional perspective view of a surgical instrument positioning device taken along the line 5—5 of FIG. 5 shown in the locked position;

FIG. 12 is a perspective view of a first leg of the surgical instrument positioning device shown in FIG. 11;

FIG. 13 is a perspective view of a second leg of the surgical instrument positioning device shown in FIG. 11;

DETAILED DESCRIPTION OF THE PREFERRED EMBODIMENTS

Figure 1:
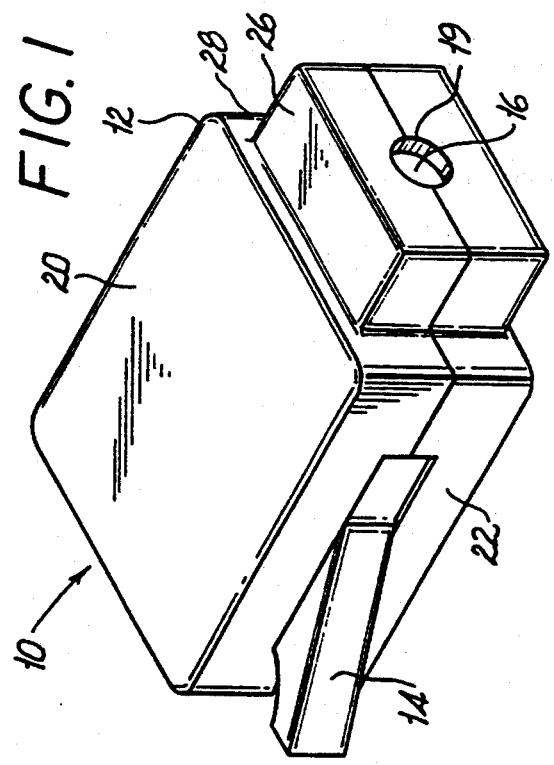
FIG. 1 is a perspective view of a surgical instrument positioning device of the present invention.

In the drawings and description which follows, the term "proximal", as is traditional, will refer to the end of the apparatus which is closest to the operator, while the term "distal" will refer to the end which is furthest from the operator.

Figure 2:
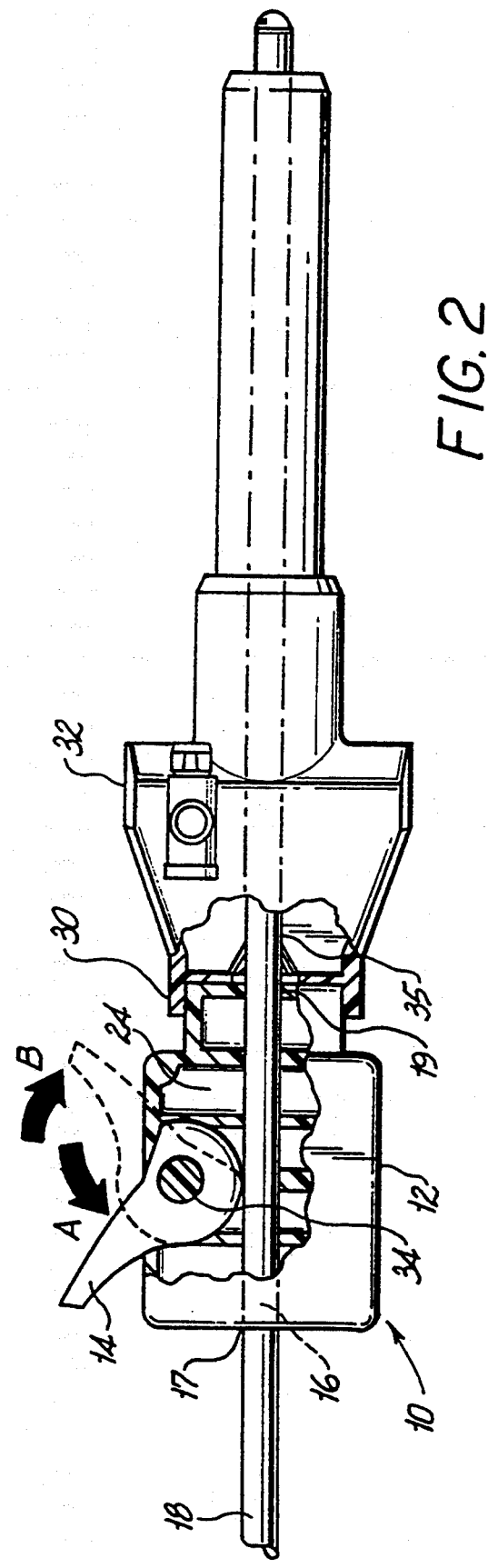
FIG. 2 is an elevational view of the surgical instrument positioning device of FIG. 1, shown mounted on a trocar cannula and having an elongated surgical instrument portion positioned therein.

Referring now to FIGS. 1 and 2 there is shown a surgical instrument positioning device 10 having a housing 12 and an actuation member 14. FIG. 2 shows the surgical instrument positioning device 12 mounted to a trocar 26 and locking the position of the elongated portion 19 of the surgical instrument (not shown), with the unlocked position of the actuating 14 lever shown in phantom. One such type of surgical instrument which could be positioned within the device 10 is the ENDO GRASP® 5 mm instrument sold by United States Surgical Corporation. More specifically, the present embodiment is preferably used for an instrument having an endoscopic portion with an outer diameter of 5 mm, although it could be designed and configured to receive various sizes. In such a case, the inner diameter of the passageway will be slightly larger than 5 mm to accomodate passage of the endoscopic portion therethrough. The device 10 includes a passageway 16 which extends along the length of the positioning device 10 and in alignment with the longitudinal axis, from a proximal opening 17 to a distal opening 19 and is dimensioned for receiving an elongated, endoscopic portion 18 of a surgical instrument. The passageway 16 of the positioning device 10 and the passageway 35 of the trocar 32 are axially aligned to ensure a continuous passage to receive the elongate instrument portion 18 of the surgical instrument.

The housing 12 includes symmetric top housing 20 and a bottom housing 22, preferably formed of a lightweight plastic material, such as LEXAN brand material manufactured by General Electric Corporation. The inner surface 24 of the top housing 20 and bottom housing 22 are contoured and recessed so as to receive the elongated portion 18 of the surgical instrument as is explained further below. The top housing 20 and bottom housing 22 are mounted to one another by sonic welding, adhesion, or other known methods of affixation.

An attachment member 26 extends from the distal end 28 of the positioning device 10 and is configured and dimensioned for insertion into and frictional engagement with the proximal end 30 of the trocar 32. While the attachment member 26 of the device 10 is shown in the drawing as having a generally rectangular configuration which conforms with the generally rectangular configuration of the proximal end 30 of the trocar 32, it should be noted that the geometric configurations of these elements could vary. For example, the attachment member 26 and the mating distal end 30 of the trocar 32 could be generally cylindrical. Also, the attachment member 26 could be threaded to engage with a matingly threaded portion of the distal end 30 of trocar 32.

The actuation member 14 is, in this embodiment, in the form of a pivotal lever, and is mounted by a pin 34 between the top housing 20 and bottom housing 22. The actuation member 14 is pivotable between a unlocked position of the actuation member 14 (shown in phantom in FIG. 2) and a locked position shown in FIG. 2. When the actuation member 14 is in its unlocked position, the elongated instrument portion 18 may pass through passageway 16 of the device 10 for insertion into or out of the positioning device 10 and trocar assembly 32. The locked position of the actuation member 14 is achieved by moving the actuation member 14 in the direction indicated by arrow A which causes the actuation member 14 to effectively reduce the size of the passageway and frictionally engage the instrument elongated portion 18 to securely maintain the instrument in position. The actuation member 14 can be returned to its initial, unlocked position by movement, in the direction indicated by arrow B, which permits the elongated instrument portion 18 to move longitudinally within both the device 10 and trocar 12.

In use, the trocar assembly 32 is inserted into the patient's body and maneuvered to the desired depth and location. The surgical instrument positioning device 10 is then mounted to the proximal end 30 of the trocar assembly 32 by fitting the attachment member 26 into the proximal end 30 of the trocar 32 for frictional engagement therein. With the actuation member 14 in its unlocked position, the surgical instrument is inserted through the proximal opening 17 of positioning device 10, through the device 10, into and through the trocar assembly 32 and maneuvered to the desired position in the patient's body. The surgical instrument is locked in the desired position by moving the actuation member 14, in the direction indicated by arrow A, from its unlocked position (shown in phantom in FIG. 2) to its locked position as shown. The actuation member 14 frictionally engages the elongated instrument portion 18 of the surgical instrument when in its locked position, thereby reliably and securely maintaining the position of the surgical instrument and enabling the surgeon or other operating room personnel to have a free hand. When the user desires to release the instrument, the actuation member 14 is pivoted by movement in the direction indicated by arrow B. The instrument elongated portion 18 may then be repositioned, or removed from the trocar assembly 32 and positioning device 10.

Referring to FIGS. 3, 3A and 3B, another embodiment of a surgical instrument positioning device 36 is provided for use with a surgical instrument. As shown, an actuation member 38 is in the form of a pivotal lever 38. Unlike the device 10 shown in FIG. 1 and which has a passageway 16 extending lengthwise through the device 10, the passageway 40 of the device 36 extends from the top housing 37 through to the bottom housing 39. FIG. 3A illustrates the actuation member 38 in its unlocked position which does not inhibit movement of the instrument elongated portion 19. FIG. 3B illustrates the actuation member 38 in its locked position which frictionally engages and restricts movement of the instrument elongated portion 19 by overlapping a portion of the passageway 40 thereby effectively reducing the size of the passageway 40 which receives the instrument elongated portion 19.

Referring to FIGS. 4, 4A and 4B, another alternative surgical instrument positioning device 40 is shown. In this positioning device 40, the actuation member 42 is pivotal along a plane lateral to the longitudinal axis of the passageway 44 and of the instrument elongated portion 19. A finger gripping portion 46 is provided on opposite sides of the housing 48 to enhance gripping and positioning of the device 40 by the user.

In use, the device 36, in its unlocked position, is positioned adjacent a trocar assembly 32 (see FIG. 2) and the surgical instrument is inserted first through the positioning device 36 and then through the trocar assembly 32. Alternatively, the elongated portion 18 of the surgical instrument may be inserted through the positioning device 36 or 40 in its unlocked position, then through the trocar assembly 32. Under either situation, the surgical instrument would be advanced to the desired location and, when desired by the user, would be locked at that desired location by moving the actuation member 38 from its unlocked to its locked position which prevents movement of the elongated portion 18 by frictional engagement therewith. The surgical instrument may be removed from the device 36 by reversing the direction of the actuation member 38 to move engagement portion 39 of the actuation member 38 away from its frictional engagement with the instrument elongated portion 18 thereby permitting movement, including adjustment or removal, of the surgical instrument from the positioning device 36. The positioning device 40 operates in a similar manner to the positioning device 36.

A further alternative embodiment is shown in FIGS. 5, 5A and 5B and is generally denominated by numeral 50. An outer housing 52 is formed by a symmetric top, outer housing 54 and a bottom, outer housing 56, both preferably formed of a lightweight plastic material as described earlier in this specification. Mounted within the outer housing 52 is a rotation knob 64 and an inner housing 58 through which the elongated portion 60 of the surgical instrument extends. The inner surfaces 57 of the top, outer housing 54 and bottom, outer housing 56 are contoured and recessed so as to receive the inner housing 58 which houses the elongated portion 60 of the surgical instrument as is explained further below. The top housing 54 and bottom housing 56 are mounted to one another by sonic welding, adhesion, or other known methods of affixation. The outer housing 54 has a slot 62 formed therein through which a rotation knob 64 extends. The outer housings 54 and 56 include a stabilizing surface 77 for stabilizing the position of the inner housing 58 positioned therein.

The rotation knob 64 is rotatably mounted within the outer housings 54 and 56 and includes a knurled surface 57 for enhanced actuation by the user. A positioning flange 59 extends from the proximal portion of the rotation knob 64 to position the knob 64 within the outer housings 54 and 56 and to facilitate insertion of, and stabilize, the surgical instrument through the opening 74. The distal surface of the rotation knob 64 includes a triangular flange 66 for engaging the inner housing 58.

The inner housing 58 includes an annular member 68, a substantially cylindrical member 70, and a generally cylindrical camming member 72. The cylindrical camming member 72, includes a camming surface 73 which engages the housing camming surface 75 formed in the inner surface 58 of the housing 54. A generally cylindrical opening 74 extends through the outer housing 54, 56, the knob 64 and along the length of inner housing 58 and is configured and dimensioned to receive the elongated portion 60 of a surgical instrument. A pair of stabilizing plates 76 extend laterally from the annular member 68 and are positioned between the stabilizing surfaces 77 extending from the inner surfaces 57 of the top housing 54 and the bottom housing 56. The stabilizing plates 76 on the annular member 68 and the stabilizing surfaces 77 cooperate to mount and fixedly position the inner housing 58 within the outer housings 54 and 56. The proximal surface of the annular member 68 has an angular surface 76 of decreasing depth formed therein for engaging the triangular flange 66 extending from the knob 64. A triangular notch 78 is also formed in the proximal surface of the annular member 68 and is configured and dimensioned to receive and engage the triangular flange 66. The annular member 68 further includes a lateral slot 80 formed distally below the triangular notch 78 to accommodate compression of the annular member 68 when the flange 66 engages the triangular notch 78. Extending longitudinally through the cylindrical member 70 and cylindrical camming member 72 of the inner housing 58 is a longitudinal slot 82 which allows compression of the cylindrical member 70 and cylindrical camming member 72 when the triangular notch 78 engages the flange 66.

The surgical instrument positioning device 50 is shown in its unlocked position in FIG. 5A. With the positioning device 50 in its unlocked position, the surgical instrument is inserted through an aperture 51 formed in the proximal surface of positioning flange 59 and housing 52 such that the device 50 is free to slide therein. The position of the surgical instrument positioned in the device 50 is locked by rotation of the knob 64 which causes the inner housing 58 to move distally in the direction indicated by the arrow D, thereby causing the camming surface 73 on the camming member 72 to engage against the camming surface 75 on the inner housing 52. The engagement of the camming surface 73 anti camming surface 75 causes the cylindrical member 70, and particularly camming member 72, to constrict inwardly and around the instrument elongated portion 60 thereby narrowing the passageway and locking the elongated instrument portion 60 therein. FIG. 5B illustrates the surgical instrument positioning device 50 in its locked position wherein the knob 64 has been rotated in the direction indicated by arrow C to cause the triangular flange 66 to travel along the angular surface 76 until the flange 66 engages the triangular notch 78; the engagement of the flange 66 on the knob 64 and the notch 78 produces an audible and tactile click sensed by the user.

Figure 6:
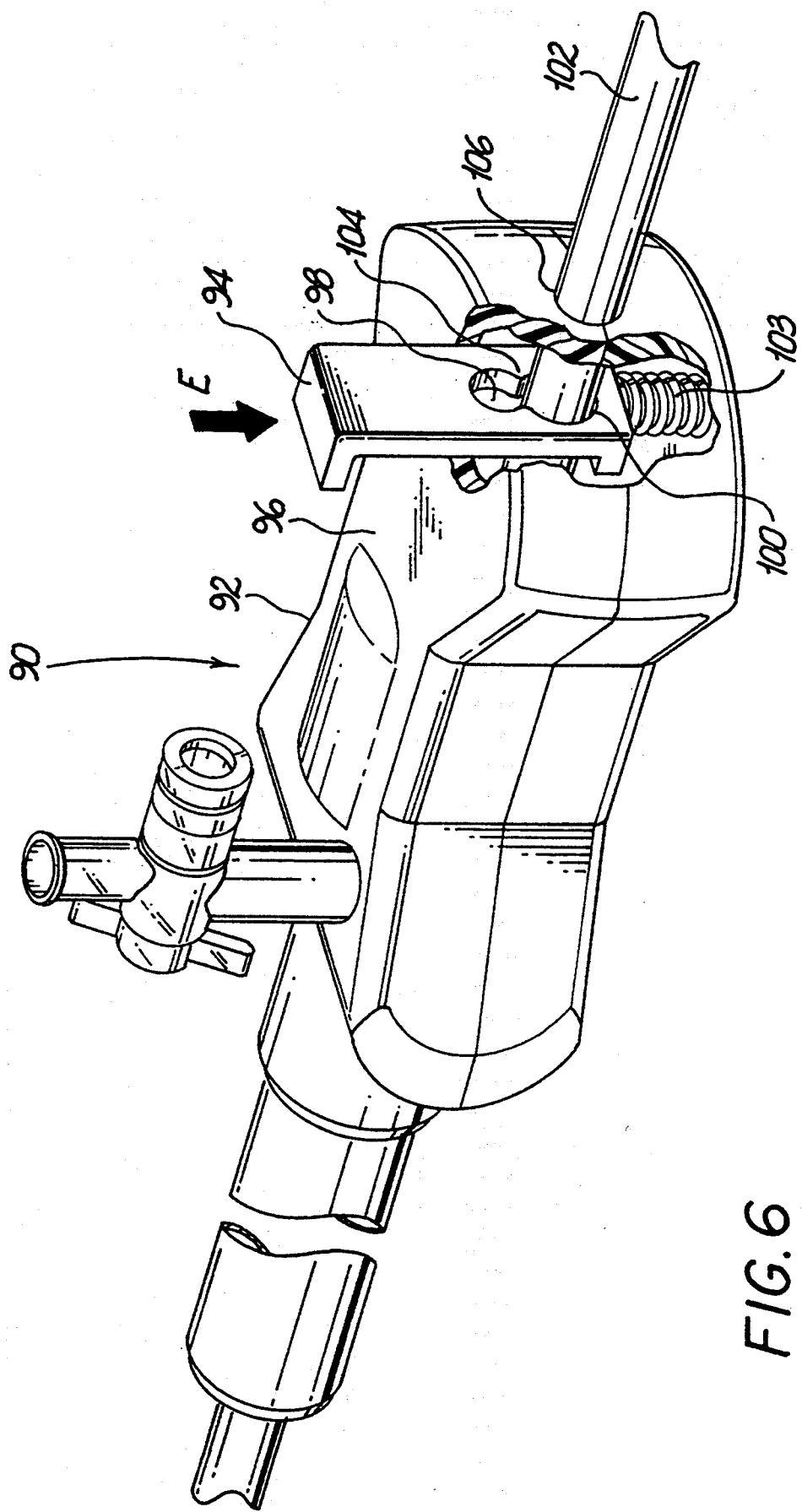
FIG. 6 is a perspective view of another embodiment of the present invention wherein a surgical instrument positioning device is integral with a trocar assembly therewith and of the type relating to the present invention.

A further alternative surgical instrument positioning device generally denominated by numeral 90 and which combines a trocar 92 and an integral positioning member 94 is illustrated in FIG. 6. In this embodiment, the positioning member 94 extends from the housing 96 of the trocar 92 and is movable between a locked and an unlocked position. The positioning member has a first, larger diameter passageway 98 and a second passageway 100 which has a smaller diameter than the first passageway 98 and which frictionally engages the instrument elongated portion 102 to lock the position thereof. A slot 104 extends and provides communication between the first passageway 98 and the second passageway 100. A spring 103 is mounted in the trocar housing 96 and biases the positioning member 94 in its unlocked position which corresponds to the first passageway 98 being concentric with the proximal opening 106 of the trocar 92.

In use, the trocar assembly 92 is inserted into the patient's body and maneuvered to the desired depth and location. The surgical instrument is then inserted through the proximal opening 106 of the trocar 92, through the first cannula 108, and positioned as desired by the user. The desired position of the surgical instrument is locked by depressing the positioning member 94 in the direction indicated by the arrow F causing the second passageway 100 to frictionally engage and retain the instrument elongated portion 102.

Figure 7:
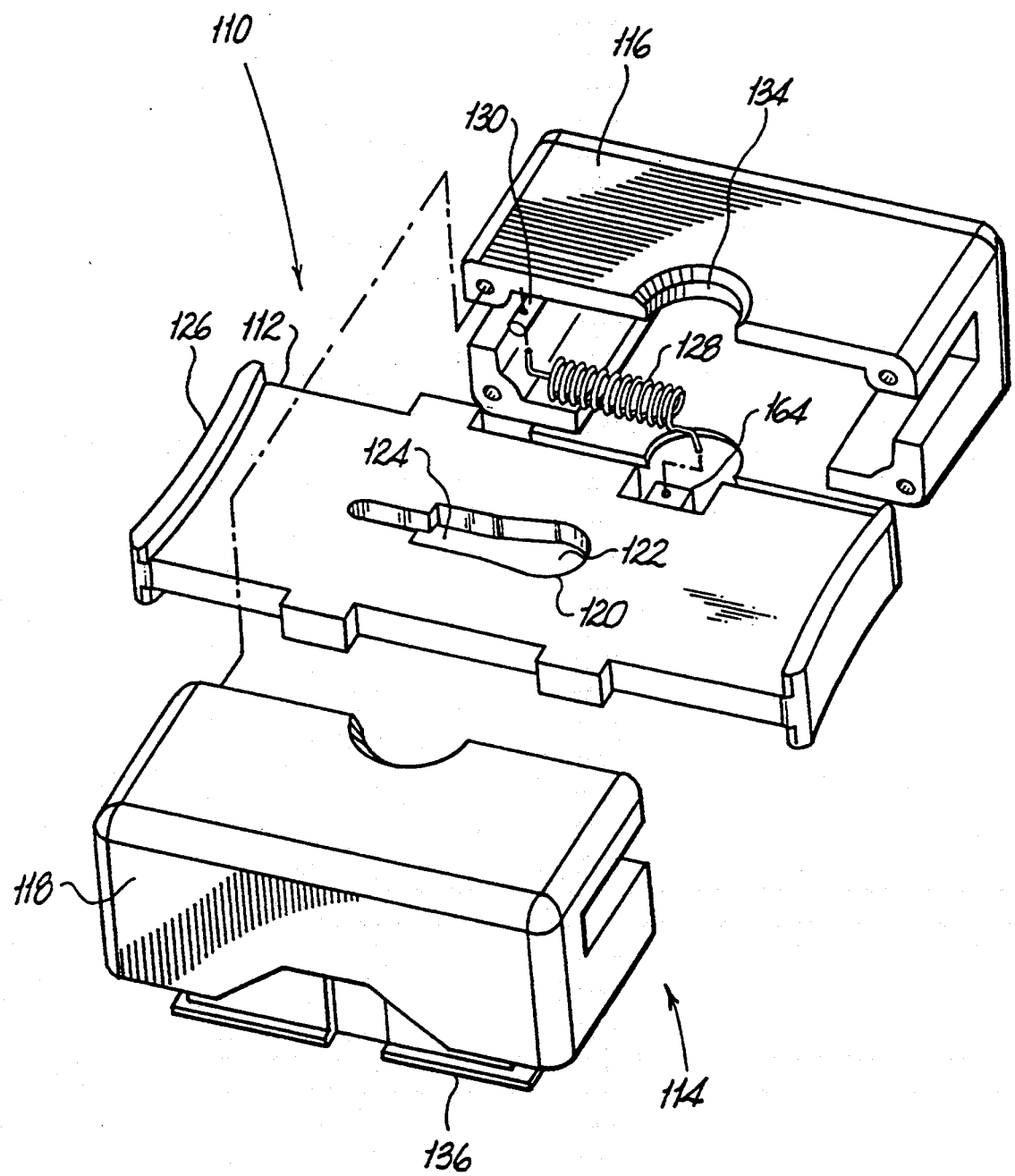
FIG. 7 is a perspective view of another alternative embodiment of a surgical instrument positioning device.
Figure 8:
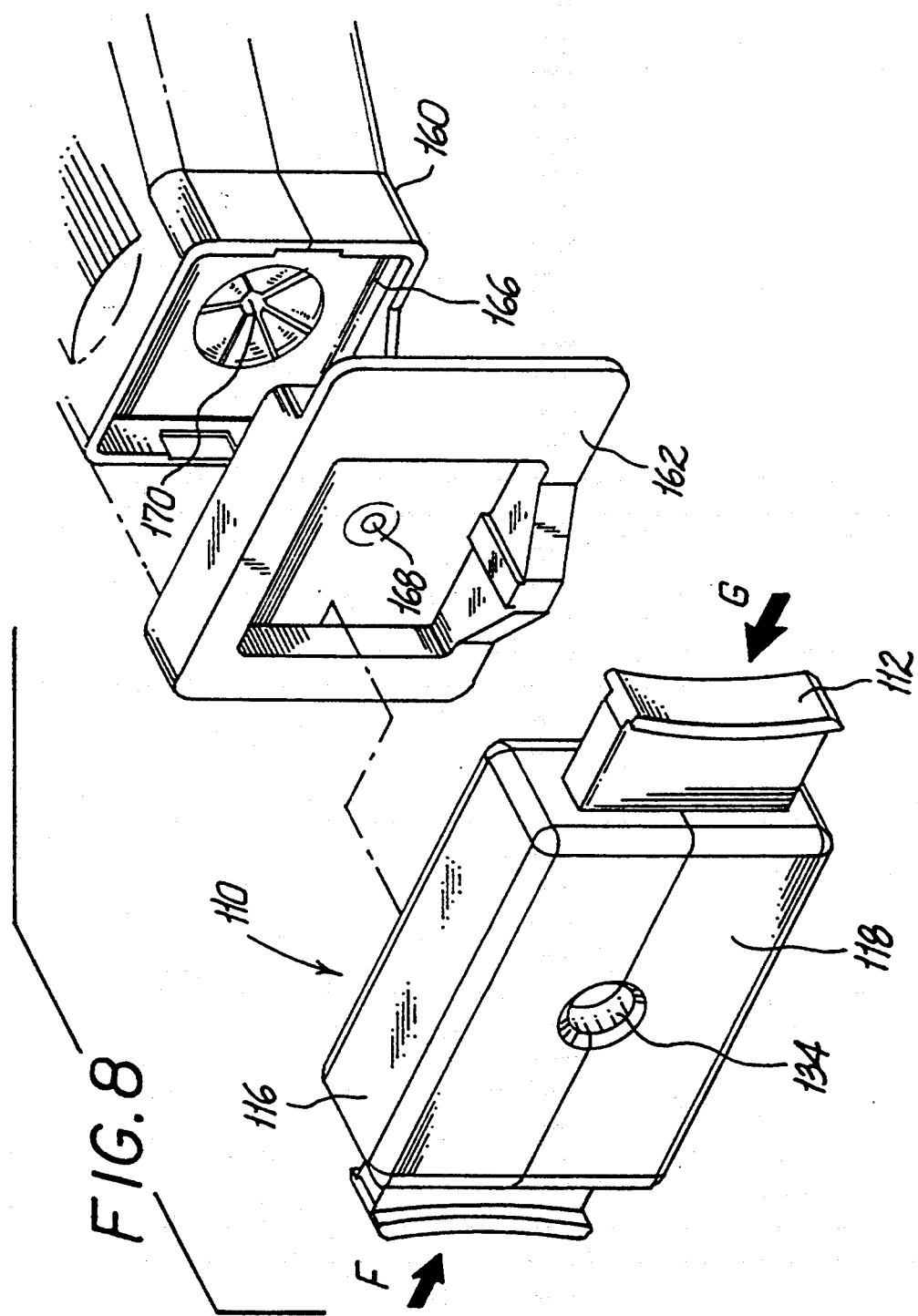
FIG. 8 is a perspective view of the surgical instrument positioning device of FIG. 7 shown in conjunction with a converter and trocar.

Yet a further alternative embodiment of surgical instrument positioning device 110 is shown in FIGS. 7 and 8. The device 110 includes a housing 114, an actuation member 112 slidably mounted within the housing 114 and a mounting member 136 configured and dimensioned to generally conform to the shape of and to mount to the proximal end 166 of a trocar 160. The housing 114 includes a top housing 116 and a bottom housing 118 which are mounted to one another in the same manner as earlier described. The actuation member 112 includes a slot 120 having a first passageway 122 which is lightly larger than the outer diameter of the instrument elongated portion to permit insertion, positioning and withdrawal of the instrument elongated portion therethrough. The slot 120 also includes a second passageway 124 in communication with the first passageway 122 and having a diameter smaller than that of the first passageway 122 to frictionally engage and lock the position of the surgical instrument retained therein. The actuation member 112 further includes finger gripping portions 126 for actuating the actuation member 112. A spring 128 biases the actuation member 112 such that the actuation member 112 is in its unlocked position and the first opening 122 is concentric and aligned with an aperture 134 of the housing 114. The spring 128 is mounted at one end to a post 164 extending from the distal surface of the actuation member 112 and is attached at its opposite end to a spring post 130 extending from the inner surface 132 of the upper housing 116.

In use, device 110 is mounted to a trocar 160 by first mounting a converter 162, for example a SURGIPORT ® converter sold by United States Surgical Corporation, to the mounting member 136 (see FIG. 7) on the distal end of the device 110. Once the converter 162 has been mounted to the positioning device 110, the converter 162 is then mounted to the proximal and 166 of the trocar 160. With the positioning device 110 in its biased, unlocked position, the surgical instrument is inserted through the housing aperture 134, through the aperture 168 of the converter 162 and through the aperture 170 of the trocar 160. The surgical instrument is then advanced to the surgical site and to the position in which the user desires to lock the instrument. The instrument is locked in position by sliding the actuation member 112 in the direction indicated by the arrow F causing the slot 120 of the actuation member 112 to move laterally along the surgical instrument elongated portion until the second aperture 124 frictionally engages the instrument elongated portion. The frictional engagement of the second aperture 124 and instrument elongated portion is greater than bias of the spring 128, thereby preventing unwanted return of the actuation member 112 to its unlocked position. The instrument may be repositioned, or removed from the surgical site, by moving the actuation member 112 in the direction indicated by arrow G causing the slot 120 of the actuation member 112 to move along the instrument elongated portion until, the first aperture 122 receives the instrument elongated portion and is concentric with the aperture 134 of the housing 114. The remainder of the device 110 is the same as previously discussed.

Figure 9:
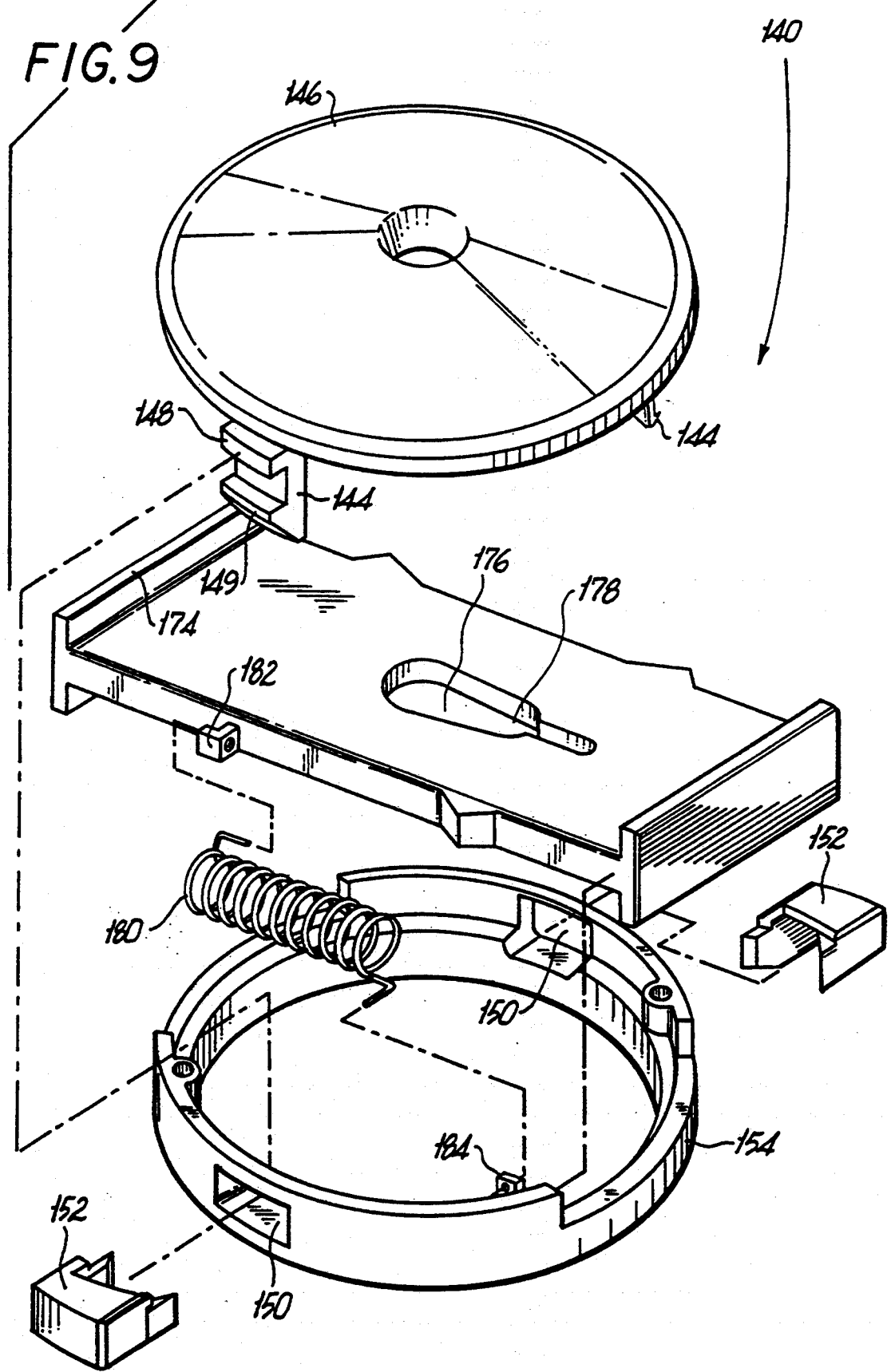
FIG. 9 is a perspective view of a further alternative embodiment of a surgical instrument positioning device.
Figure 10:
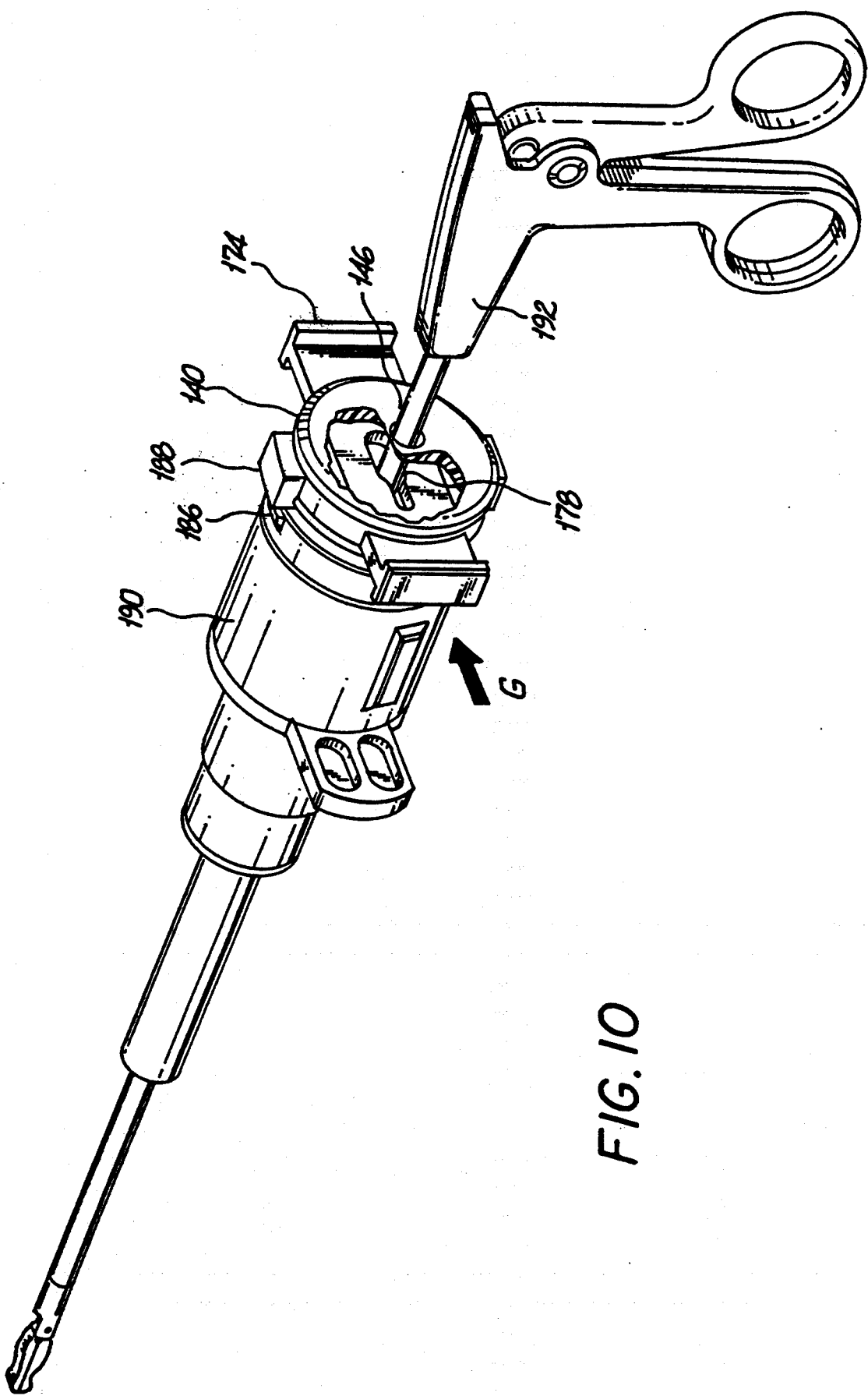
FIG. 10 is a perspective view of the surgical instrument positioning device of FIG. 9 shown mounted on a trocar cannula and having an elongated surgical instrument positioned therein.

Another alternative embodiment of a device generally designated by the numeral 140 for positioning a surgical instrument is shown in FIG. 9, and is also shown in FIG. 10 locking the position of surgical instrument 192 positioned therein. The positioning device 140 is configured and dimensioned for use with a trocar, such as the PREMIUM SURGIPORT trocar sold by United States Surgical Corporation and which has a generally cylindrical proximal end 142 as is shown in the drawings.

The device 140 includes a top housing 146, a bottom housing 154 and a slidable actuation member 174 mounted therebetween and having a first aperture 176 and a second, smaller aperture 178 positioned therebetween. A spring 180 is mounted at one end to a spring post 182 on the actuation member 174 and at an opposite end to a spring post 184 extending from the bottom housing 154. The bottom housing 154 may be attached to the top housing 146 by sonic welding, an adhesive or any other known means of attachment. The positioning device 140 also includes a pair of legs 144 which extend from the top housing 146 and include a pair of first engagement tabs 148 for engaging a pair of cooperating slots 150 formed in the bottom housing 154. A second pair of slots 186 are formed in the proximal end 188 of the trocar 190 for receiving a second pair of engagement tabs 149 which extend from the legs 144. The second pair of engagement tabs 149 engage the second pair of slots 186 formed in the proximal end 188 of the trocar 190 to mount the positioning device 140 to the trocar 190. A pair of release members 152 are mounted within the bottom housing 154 and engage against the legs 144 to release the legs 144 from their engagement with the slots 150 when the release members 152 are pressed inwardly. The remainder of the device 140 is the same as previously discussed.

Figure 11:
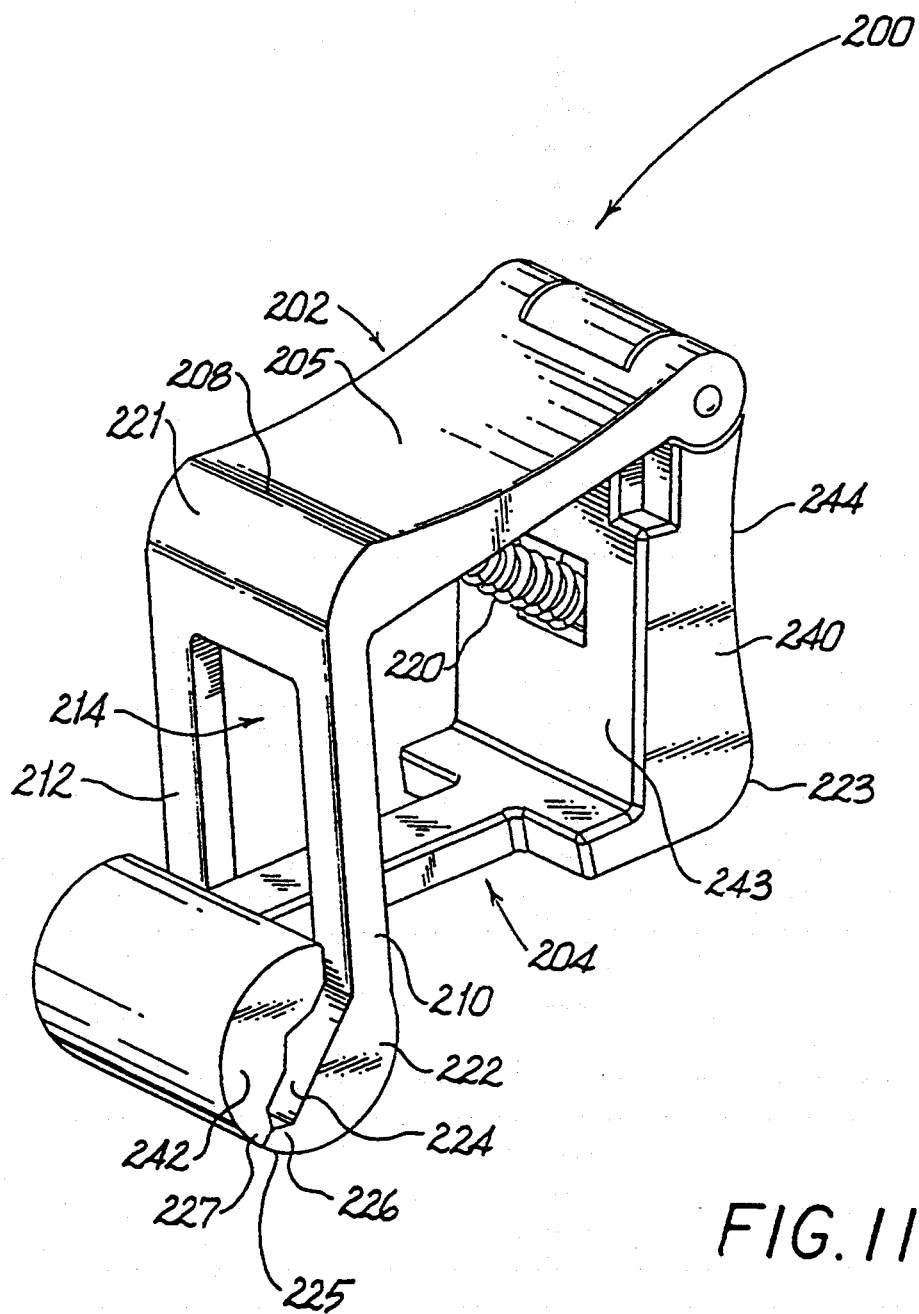
FIG. 11 is a perspective view of a further alternative embodiment of a surgical instrument positioning device.

Yet another alternative embodiment of a device for positioning a surgical instrument is shown in FIGS. 11 to 13 and is generally designated by the numeral 200. The device 200 includes a first leg 202 and a second leg 204 pivotally attached thereto, the legs 202, 204 being constructed of any suitable material, for example, a plastic material. The first and second legs 202, 204 each include a squeeze portion 208 for squeezing by the user to move the legs 202, 204 relative to each other.

The upper portion of the first leg 202 includes a pair of oppositely positioned, cylindrical pin retainers 230 and 232 which receive a pin 206. The pin retainers 230, 232 are configured and dimensioned to receive the pin retaining member 228 of the second leg 204 therebetween and further to receive the pin 206 which extends through the pair of pin retainers 230, 232 and pin retaining member 228. A recessed portion 234 is formed between the pin retainers 230, 232 of the squeeze portion 208 to accommodate the base 236 of the pin retaining member 228.

As best shown in FIG. 12, a spring post 216 extends from the inner surface 218 of squeeze portion 208 of the first leg 202 for engaging a spring 220, which is preferably a coil spring, for biasing the squeeze portions 208 of the legs 202, 204 in a direction away from each other. The first leg 202 has a pair of arms 210 and 212 extending at an angle from the squeeze portion 208. The outer surface 226 of the squeeze portion 208 is contoured to enhance actuation of the squeeze portion 208 by the user. An opening 214 is formed between the arms 210, 212 and is configured and dimensioned to receive the clamping member 242 of the second leg 204 therethrough during assembly. A clamping member 222 having a relatively flat clamping surface 224 and a rounded outer surface 225 extends from the arms 210, 212. The clamping surface 224 provides a surface for clamping and engaging an elongated portion of a surgical instrument to lock the position thereof. The damping member 222 terminates in an engagement member 226 which engages with the engagement member 227 of the second leg 214 to retain the legs 202, 204 against themselves and against the bias of the spring 220.

The second leg 204 is configured similar to the first leg 202 and includes an actuation member 240 having an inner surface 243 and an outer surface 244. An arm 246 is angled relative to and extends from the lower portion of the actuation member 240 and is configured and dimensioned to be slidably received within the opening 214 between the arms 210, 214 of the first leg 204. A clamping member 242 extends from, and at an angle relative to, the arm 244 and includes a clamping surface 246 which works in combination with the clamping surface 224 of the first leg 202. A concave portion of V-shaped notch 248 is formed laterally in the clamping member 242 and in the clamping surface 246 and enhances gripping by increasing the number of contact points of the clamping surface 224 and 246. A rubber pad 248, formed of Santoprene or other elastomeric material, may be adhered by an adhesive to each of the clamping surfaces 224 and 246 to further enhance the gripping of these surfaces. The clamping members 222 and 242 are movable between a first position where the engagement members 226, 227 are movable between a first position where the engagement members 226, 227 are biased by the spring 220 against each other, and a second position where the bends 221,223 of the first leg 202 and second leg 204 are approaching each other and a first opening 229 is created between the engagement members 226, 227 and second opening 231 is inserted between the clamping members 224, 242.

In use, for example in a laparoscopic procedure, a trocar is placed into a patient and a surgical instrument is inserted through the trocar cannula assembly and advanced to its desired position. The positioning device 200 may then lock the position of the surgical instrument in that desired position by first squeezing together the actuation members 226 and 240 of the first and second legs 202 and 204, respectively, to overcome the bias of spring 200 and to move the clamping members 222 and 242 to their open position and around the elongated portion of the surgical instrument. To lock the position of the surgical instrument, the device 200 must be positioned adjacent the trocar cannula assembly which provides a base for preventing movement of the device 200 further in the direction of the surgical site. When the positioning device has been properly placed relative to the trocar assembly and around the elongated portion of the surgical instrument, the actuation members 226 and 240 may be released thereby allowing the legs 202 and 204 and clamping numbers 224 and 242 to return to their biased and closed position with the elongated instrument portion securely gripped by the clamping members 224 and 242.

Figure 14:
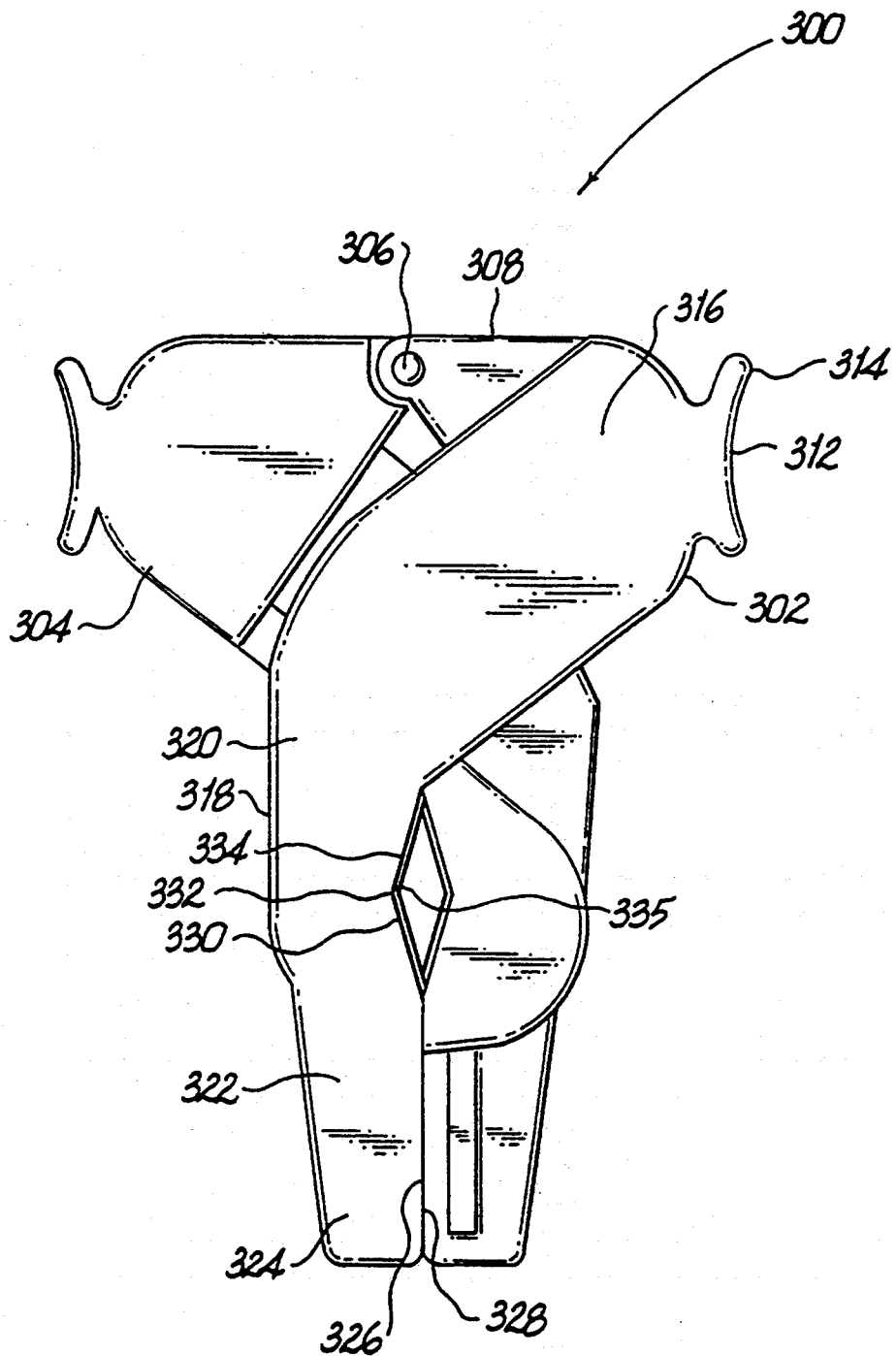
FIG. 14 is a perspective view of yet an additional embodiment of a surgical instrument positioning device.
Figure 15:
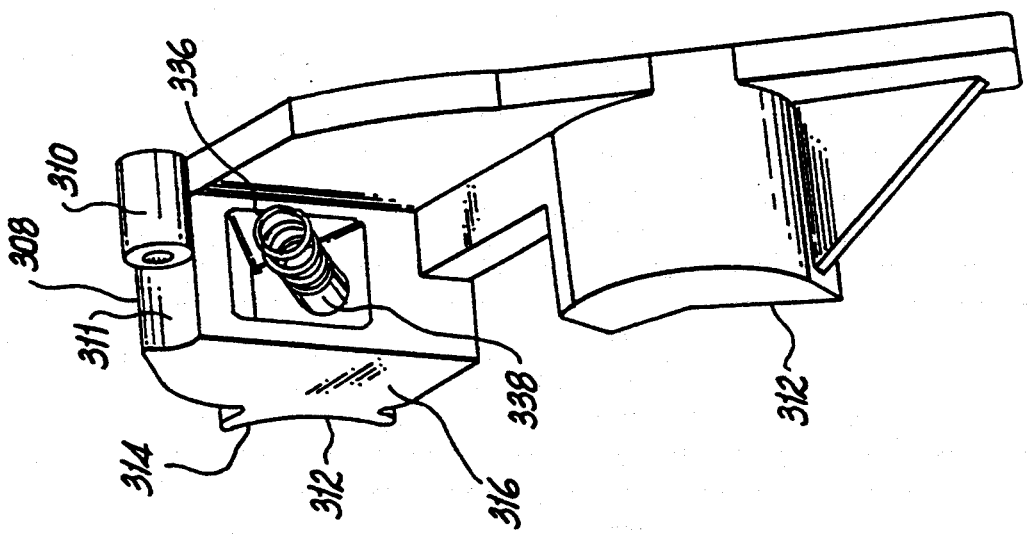
FIG. 15 is a perspective view of the leg of the surgical instrument positioning device shown in FIG. 14.

A further alternative embodiment of a device for positioning a surgical instrument is shown in FIGS. 14 and 15 and is generally designated by the reference numeral 300. The device 300 includes a first leg 302 and a second leg 304 pivotally connected by a pin 306, although the legs 302, 304 could also be integral. Since the legs 302 and 304 are identical parts, only one leg 302 will be discussed. A spring 336, which is preferably a coil spring, is mounted to a spring post 338 which extends from an inner surface 340 of the shoulder 316. The first leg 302 has a top surface 308 from which extends a substantially cylindrical, pin receiving member 310. The second leg 304 also includes a substantially cylindrical pin receiving member which is received in a recess 311 of the first leg 302. An actuation surface 312 which in this embodiment is rounded and includes tabs 314 extends laterally from the shoulder 316 of the first leg 302. An arm 318 extends from the shoulder 316 and includes a first member 320 also angled relative to the shoulder 316 and a second member 322 which is angled relative to first member 320. The arm 318 terminates in a engagement portion 324 having an engagement surface 326 to engage against the engagement surface 328 of the second leg 304. The inner surface 330 of the arm 318 includes a substantially V-shaped clamping member 332 having a clamping surface 334 for gripping the elongated portion of the surgical instrument. A rubber pad 335 may be adhered to the damping member 332 to enhance the gripping and clamping of the clamping surface 334. The remainder of the device is the same as described for the previous embodiment.

Referring to FIG. 20, the surgical instrument positioning device 300 is shown positioning a surgical instrument 301 having an elongated portion 303 relative to a trocar cannula assembly 305 and further relative to a surgical site. In use, the device 300 is positioned adjacent a trocar 305 and around the elongated portion 303 of a surgical instrument 301 by squeezing the actuation surfaces 312 of the legs 302, 304 toward each other thereby overcoming the bias in spring 336 to create an opening sufficient to receive the elongated portion 303 of the surgical instrument 301. Release of the actuation surfaces 312 causes the clamping surfaces to clamp around the elongated portion 303 and lock its position relative to the trocar cannula assembly 305.

Figure 16:
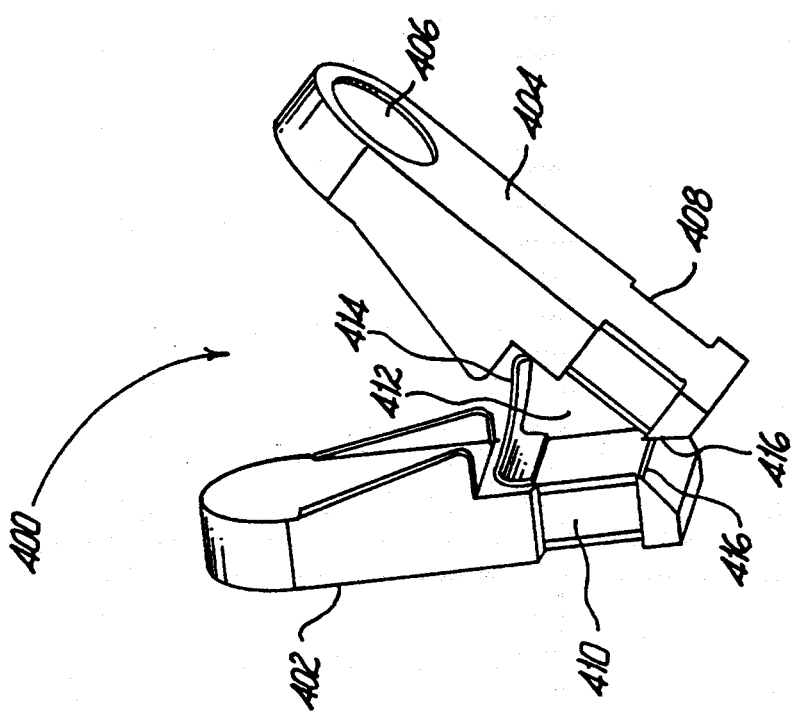
FIG. 16 is a perspective view of a further alternative embodiment of the surgical instrument positioning device.

A further embodiment of a surgical instrument positioning device is shown in FIG. 16. In this positioning device 400, the legs are elongated and of slender construction and are identical in this embodiment. Each leg 402, 404 includes an squeeze portion 406 for enhanced movement of the legs 402, 404 by the user. The bottom portion of each of the legs 402, 404 includes a recessed portion 408 configured and dimensioned to receive an attachment member 410 which, in this embodiment is a leg spring, and is bent around the recessed portion 408 of the legs 402, 404. The attachment member 410 attaches the legs 402, 404 to one another and also biases the engagement portions 416 of each of the legs against each other. A gripping portion 412 is formed by a cavity and in the inner surface 414 of the attachment member 410. An engagement portion 416 is formed in the bottom surfaces of each of the legs 402, 404 which engage against one another in that portion.

Figure 18:
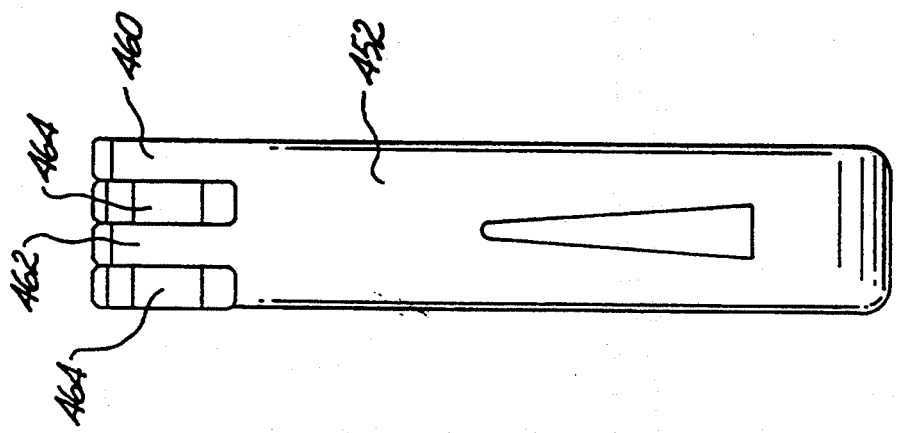
FIG. 18 is a side view of the positioning device shown in FIG. 17.
Figure 17:
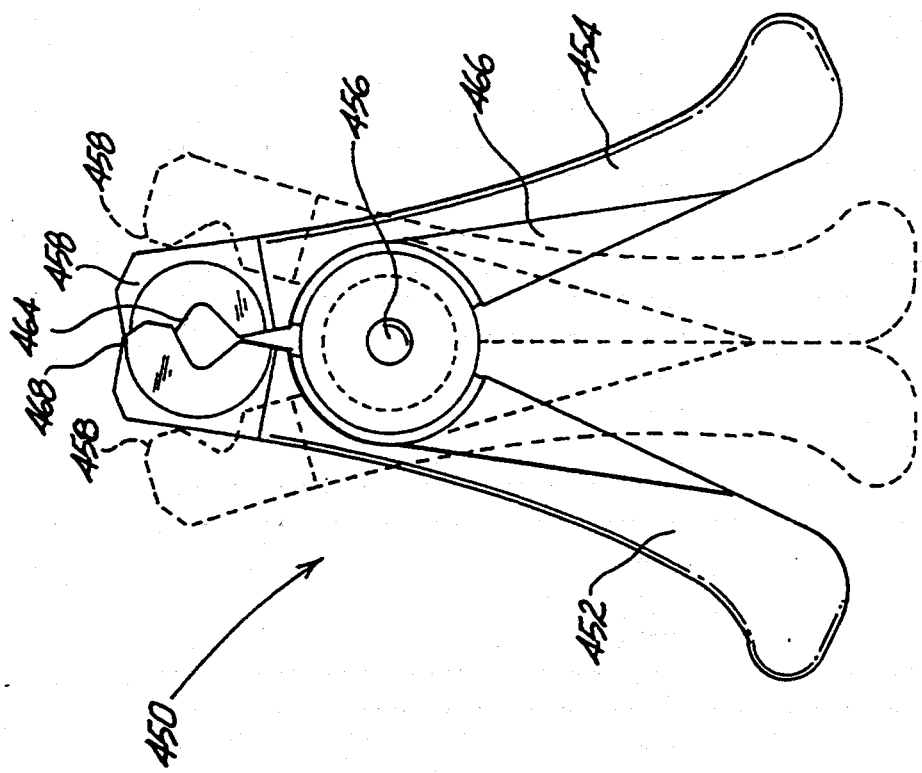
FIG. 17 is a front view of yet a further alternative embodiment of a surgical instrument positioning device.
Figure 19:
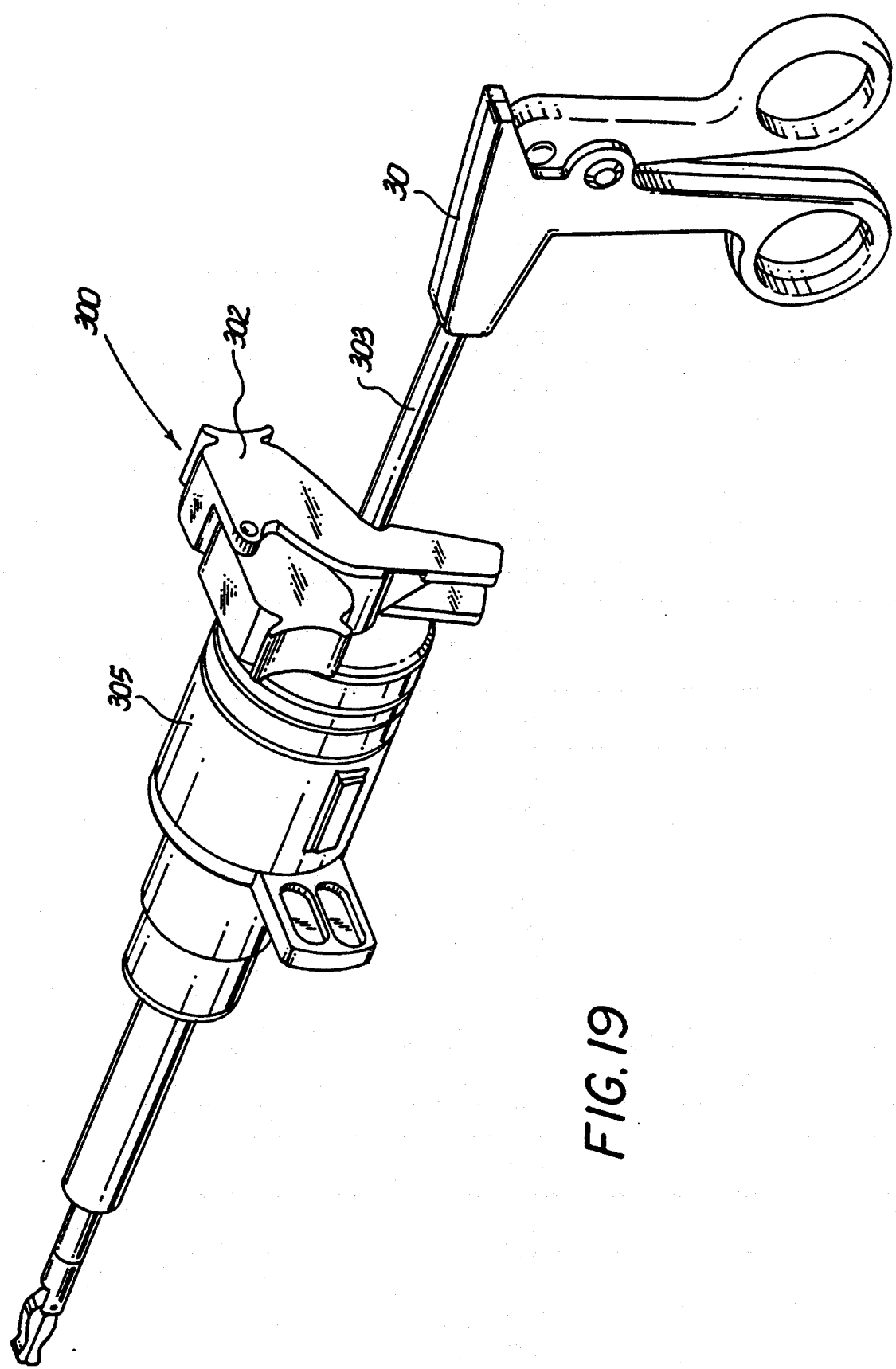
FIG. 19 is a perspective view of the positioning device of FIG. 16 shown mounted adjacent a trocar cannula and having an elongated surgical instrument positioned therein.

Refering to FIGS. 17 and 18, yet a further embodiment of the surgical instrument positioning device 450 is shown. In this positioning device a pair of legs 452, 454 pivot about a pivot pin 456 and which overlap at an overlap portion 468. Each leg 452, 454 includes a clamping member 458 which preferably is formed by a pair of clamping arms 460, 462 which form a gripping portion 464 configured and dimensioned to grip the elongated portion of a surgical instrument therein. A spring 466, which in this case is a tension spring, biases the clamping members 450 of each of the legs 452, 454 into engagement. The positioning device 450 is shown in phantom in FIG. 17 in its opened positioned wherein the legs 452, 454 have been squeezed to overcome the bias of the spring 466.

While the invention has been particularly shown and described with reference to the preferred embodiments, it will be understood by those skilled in the art that various modifications and changes in form and detail may be made therein without departing from the scope and spirit of the invention. Accordingly, modifications such as those suggested above, but not limited thereto, are to be considered within the scope of the invention.

What is claimed is:

1. A device for positioning a surgical instrument having an elongated portion within a trocar, the device comprising:
   a first and a second leg pivotally connected at a first end and movable between a first and a second position;
   a biasing means mounted to said first and second legs for biasing said legs relative to each other and into said second position;
   an aperture positioned between said first and second legs for receiving the elongated portion of the surgical instrument; and
   an engagement portion associated with said aperture for frictionally engaging a portion of said instrument elongated portion to prevent movement of the instrument portion positioned therein:
   wherein said device is mounted to a proximal end of the trocar.

2. A positioning device as in claim 1 wherein said elongated instrument portion is frictionally retained within said aperture when said legs are in said second position.

3. A positioning device as in claim 1 wherein said first and said second legs each have a leg retaining member such that said leg retaining member of said first leg engages against said leg retaining member of said second leg to frictionally retain said first and second legs relative to each other.

4. A positioning device as in claim 1 wherein a portion of said legs overlap.

5. A positioning device as in claim 1 further comprising engaging pads mounted to said engagement portion of said legs for enhancing engagement of the elongated instrument portion positioned in said aperture.

6. A positioning device as in claim 5 wherein said engaging pads are formed of a rubber material.

7. A positioning device as in claim 1 wherein said first and second legs each have an actuation portion for moving said first and second legs between said first and second positions.

8. A positioning device as in claim 7 wherein said actuation portions and the mounting of said biasing means are oppositely positioned relative to each other on said first and said second legs.

9. A positioning device as in claim 1 wherein said biasing means is encased within said first and second legs.

10. A positioning device as in claim 1 wherein said biasing means is a coil spring.

11. A positioning device as in claim 1 wherein said biasing means is a leaf spring.

12. A positioning device as in claim 11 wherein said biasing means is configured to form said aperture which receives said elongated portion.

13. A positioning device as in claim 1 wherein said first and second legs are integral.

* * * * *